United States Patent
Garito et al.

(10) Patent No.: US 6,620,156 B1
(45) Date of Patent: Sep. 16, 2003

(54) BIPOLAR TONSILLAR PROBE

(76) Inventors: Jon C. Garito, 1135 Railroad Ave., Hewlett, NY (US) 11557; Alan G. Ellman, 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 10/246,919

(22) Filed: Sep. 20, 2002

(51) Int. Cl.$^7$ ............ A61B 18/14; A61N 1/05
(52) U.S. Cl. ............ 606/32; 606/41; 606/48; 606/50; 607/99; 607/113
(58) Field of Search ............ 606/32, 34, 40, 606/41, 48, 50; 607/99, 113

(56) References Cited

U.S. PATENT DOCUMENTS

| | | | | | |
|---|---|---|---|---|---|
| 1,814,791 A | * | 7/1931 | Ende | ............ | 606/50 |
| 1,916,722 A | * | 7/1933 | Ende | ............ | 606/50 |
| 1,943,543 A | * | 1/1934 | McFadden | ............ | 606/49 |
| 2,611,365 A | * | 9/1952 | Rubens | ............ | 606/42 |
| 5,403,311 A | * | 4/1995 | Abele et al. | ............ | 606/50 |
| 5,683,386 A | * | 11/1997 | Ellman et al. | ............ | 606/41 |
| 5,868,744 A | * | 2/1999 | Willmen | ............ | 606/50 |
| 6,106,521 A | * | 8/2000 | Blewett et al. | ............ | 606/41 |
| 6,387,093 B1 | * | 5/2002 | Ellman et al. | ............ | 606/39 |

* cited by examiner

*Primary Examiner*—Lee Cohen

(57) ABSTRACT

An RF tonsillar probe comprises a generally elongated insulated structure having means for coupling to the bipolar outlet of electrosurgical apparatus, and two internal insulated wires leading to a distal end that is angled downwardly and that terminates in two laterally-spaced needle electrodes whose tips are exposed. The probe works best with relatively high-frequency RF electrosurgical currents in excess of 1.5 MHz. The combination of the bipolar mode with electrosurgical currents in the MHz range causes relatively low tissue temperatures avoiding the need for the addition of a complicated temperature-controller structure and suitable circuitry, and the bipolar action confines the RFTA effect to the tissue region between the two active needle electrodes.

12 Claims, 3 Drawing Sheets

BIPOLAR TONSILLAR PROBE

This invention relates to a bipolar tonsillar probe for tonsil reduction with radio frequency energy in an electrosurgical procedure.

BACKGROUND OF THE INVENTION

Our prior U.S. Pat. No. 6,387,093, whose contents are hereby incorporated by reference, describes a novel electrode and electrosurgical procedure for treating Obstructive Sleep Apnea Syndrome (OSAS) by Radio Frequency Thermal Ablation (RFTA), which uses radio frequency (RF) heating to create targeted tissue ablation resulting in tissue volume reduction of tongue base tissue. This procedure uses a unipolar electrode.

Children having tonsillar problems, such as enlarged tonsils, are conventionally treated by removal of the tonsils. However, it-has been suggested recently that such a procedure (tonsillectomy usually accompanied by adenoidectomy) can be replaced with a procedure which involves no surgery, produces minimal post-procedure pain, and shortens the recovery period. This new procedure involves temperature-controlled RF submucosal tissue volume reduction, using relatively low frequency electrosurgery (in the low KHz range) and also a unipolar electrode with the conventional ground plate.

It has been our experience that low frequency electrosurgery inherently tends to produce high temperatures in the tissues treated; thus the need for the temperature-controller. Moreover, the need for the temperature-controller leads to a more complex structure of the electrosurgical electrode.

SUMMARY OF THE INVENTION

The present invention describes a novel RF tonsillar probe that can be used with low power electrosurgical apparatus for the purpose of implementing RFTA with a relatively simple, easily learned procedure.

Briefly stated, the novel probe comprises a generally elongated insulated structure having at a proximal end a cable connector for coupling to the bipolar outlet of electrosurgical apparatus, two internal insulated wires leading from the cable to a distal end that is angled downwardly and that terminates in two laterally-spaced needle electrodes whose tips are exposed. Our novel probe works best with relatively high-frequency RF electrosurgical currents in excess of 1.5 MHz, preferably in the range of 1.5–4 MHz. We have found that the combination of the bipolar mode with electrosurgical currents in the MHz range causes relatively low tissue temperatures avoiding the need for the addition of a complicated temperature-controller structure and suitable circuitry, and the bipolar action confines the RFTA effect to the tissue region between the two active needle electrodes. The downwardly-extending distal end housing the two needle electrodes also simplifies for the surgeon placement of the needle electrodes at the tonsil site where the volumetric shrinkage is desired. The downward angle preferably is about 60°–90°, preferably about 75°. Preferably, the needle portions adjacent the distal end are covered with a thin electrically-insulating coating to prevent electrosurgical currents from entering the tonsil tissue except from the needle tips.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

The reader is directed to the referenced prior patent which will assist in understanding the improvements offered by the present application.

As mentioned, low-power electrosurgical apparatus is needed. Such apparatus is available from Ellman International of Hewlett, N.Y. as Model IEC50. In this case, the typical electrosurgical handpiece has been integrated with the active electrodes which is the preferred embodiment, but, in principle, the electrode part can be manufactured as a separate entity and mounted in a handpiece that will provide side-by-side bipolar currents to the working end.

Figure 1:
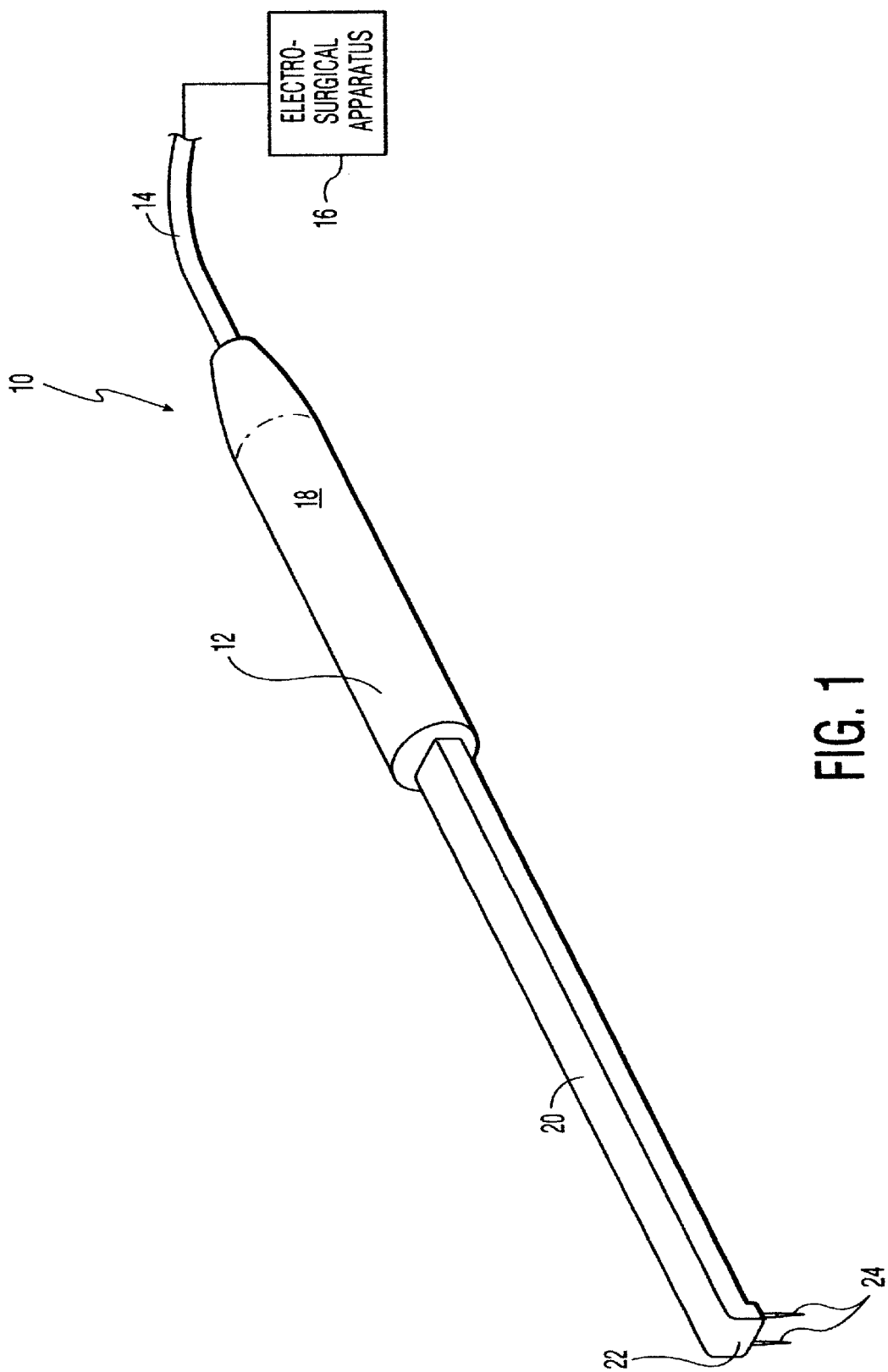
FIG. 1 is a perspective view of one form of an RF tonsillar probe in accordance with the invention shown connected to suitable electrosurgical apparatus.

In the preferred embodiment of a probe according to the invention illustrated in FIG. 1, the probe 10 comprises an elongated handle part 12 out of the proximal end at the right extends a bipolar cable 14 which is supplied with a standard electrical connector (not shown) for plugging into the bipolar outlet of the electrosurgical instrument 16. The handle part 12 comprises a widened section 18 followed by a narrower section 20 which at its distal end forms a downwardly-extending, preferably at right angles, distal end 22 from which project downwardly the two active laterally-spaced needle electrodes 24.

Figure 2:
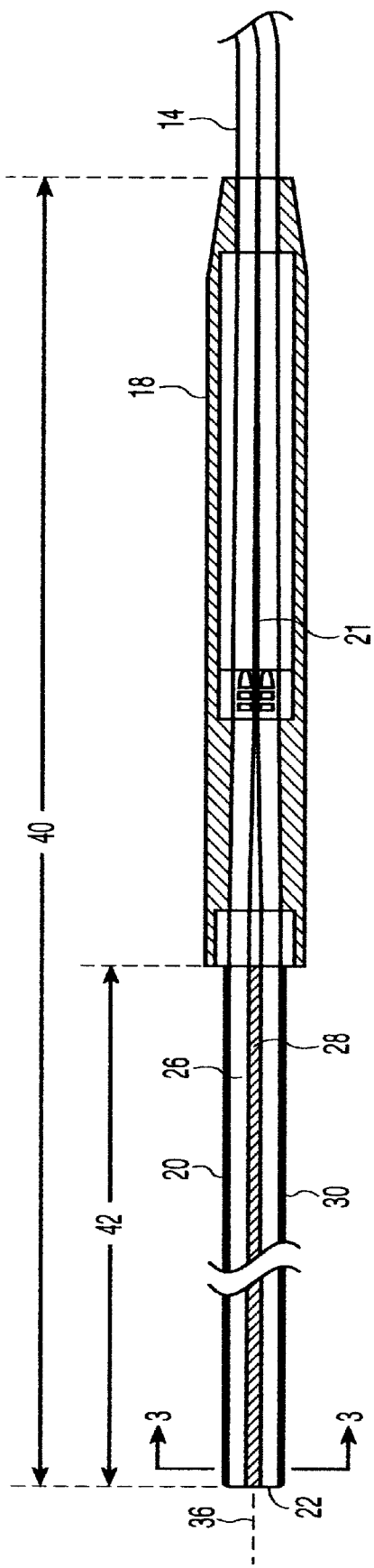
FIG. 2 is a top view of the probe of FIG. 1.
Figure 3:
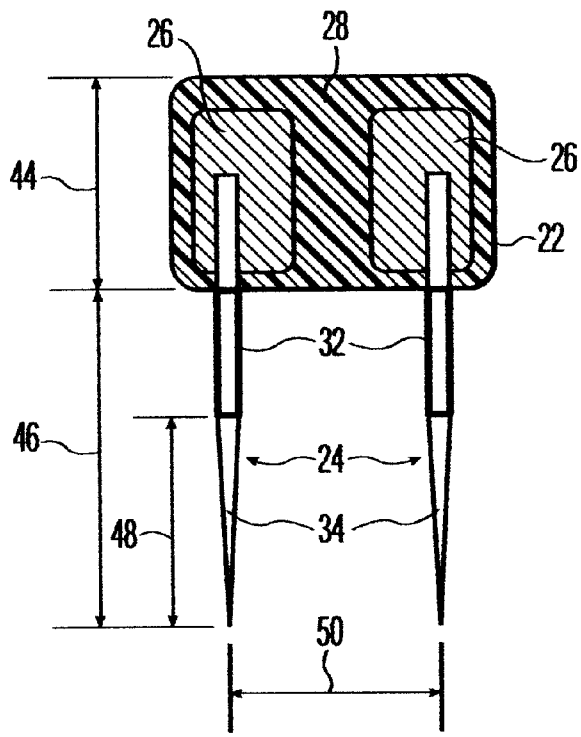
FIG. 3 is a cross-sectional along the line 3—3 of FIG. 2.

The structure of the probe preferably comprises as illustrated in FIGS. 2 and 3 a wider handle part 18 made of a suitable electrically-insulating plastic material to which is integrally mounted the narrower part 20. The cable 14 is secured to the proximal end of the handle (the end electrically closest to the electrosurgical apparatus 16) and forms on the interior of the handle two electrically-insulated wires 21 that are connected on the interior to laterally-spaced and electrically-insulated metal tubes 26 which extend through the narrower part 20 to the distal end 22. The metal tubes 26 are electrically isolated within the narrower part by an electrically-insulating partition 28, and the narrow part 20 is also coated with a thin layer of an electrically-insulating coating 30. At the distal end 22, the two metal needle electrodes 24 are respectively embedded into each of the tube ends and thus are electrically connected to the tubes 26, preferably of brass. The needle electrodes 24 from where they exit the narrower part of the handle 20 are coated with a thin layer 32 of electrically-insulating material, such as Teflon. The coating 32 is shown in FIG. 3 by slightly thicker lines. The remainder of the needles, below the coated part 32, preferably of tungsten, are tapered down 34 to a very sharp point as small as possible to concentrate the currents at the needle tips. The tapered sections 34 are bare and free of any electrically-insulating coatings. Preferably, the length of the bare needle section 34 is about 1.3–1.7 cm, preferably about 1.5 cm. The anatomical depth of the human tonsil is approximately 2 cm; hence the preferred depth of insertion of the active needles is about 1.5 cm. The coated sections of the needles protect from injury to other organs of the oral cavity. In the embodiment illustrated, the needles 24 preferably extend in a common plane which is perpendicular to the common axis 36 of the handle parts.

For a clearer understanding of the structure, preferred dimensions are as follows.

The straight handle sections 18, 20 can have an overall length 40 of about 7.0–9.0 inches, and the length 42 of the narrower handle part 20 is about 3.50–4.5 inches. The height 44 of the distal end 22 is about 0.2 inches. The parallel needles 24 project downward below the distal end a distance 46 of about 1.0–0.75 inches, and the bare tapered points 34 are preferably of the same length 48 of about 0.6–0.65 inches each. The lateral needle spacing 50 is about 0.15–0.25 inches. The metal tubes can each be a 3/32 inch brass tube, which is sufficiently stiff and strong that it will withstand excessive flexing and hold its shape when the needle ends are pushed into tissue. The orientation of the needles are not meant to be adjustable by the surgeon. The needle points 34 at the bare end must be sufficently sharp so that they can easily penetrate tonsil tissue as deep as necessary during the procedure without causing undue strain on the surgeon. The insulation of the thin electrically-insulating coating 32 must be capable of not fracturing during the procedure to avoid RF leakage that could create ulceration, as well as be normally capable of resisting RF leakage when whole, yet must be sufficiently smooth so as not to create undue friction between it and the tissue as the needles penetrate the tissue. The needle outside diameter must be small enough to enable easy penetration into the tissue yet large enough to withstand the flexing forces involved in the penetration. A size between about 0.015–0.03 inches is suitable. The sharpened ends 34, again for easy penetration, preferably taper to a sharp point over the distance previously indicated.

The appearance of the coated needle sections 32 are easily visually distinguished from the bare needle ends 34 so that the surgeon is able to readily determine the depth of tissue penetration.

The surgical procedure is as follows. Only the steps relative to the invention are recited in broad terms. The bipolar probe 10 is connected in the usual way to the electrosurgical apparatus 16. The surgeon inserts the handle 12, needle ends 24 first, into the tonsil of the patient, to a depth substantially equal to the length of the bare needle ends 34. The surgeon then activates the electrosurgical apparatus 16 choosing operating parameters such that relatively low power, low voltage settings of the apparatus are chosen. For the IEC50 instrument, which generates an output power of about 50 watts, a typical power setting of about 3–8 can be used. These values can be determined beforehand using test tissue, typically animal, and measuring the temperature due to resistive heating in the tissue surrounding the tip of the needle after a reasonable ON time of the instrument, say about 8–20 sec. The goal should be a low tissue temperature of about 50° C., at which temperature the tissue between the inserted needle sections 34 carbonizes as a result of the bipolar currents. When the needles are withdrawn, scar tissue is formed which ultimately becomes absorbed by the body shrinking the tissue volume. This normally will shrink the tonsil tissue alleviating the symptoms. If more shrinkage would be required than can be obtained from a single treatment, before or after the apparatus has been turned off and while, the tissue remains heated or is allowed to cool down if desired, the surgeon can insert the needles in another tonsil section and repeat the procedure, the resistive heating occurring in a second area around the bare needle ends 34. No heating occurs around the coated sections 32 if they also penetrate, because they are adequately electrically-insulated and no electrosurgical currents flow into the tissue from those coated section 32. The simplicity of the procedure is evident. The difference between the tissue shrinkage process and a typical electrosurgical cutting is that, with the latter, the surgeon uses the activated electrode for the shortest time possible while cutting to avoid extensive tissue damage, while, with the tissue shrinkage procedure, the active electrode stays in the tissue a reasonable time at each penetration to ensure that extensive tissue damage will occur, since it is only the damaged tissue that will shrink.

The insulating handle part 20 will prevent accidental touching of patient tissue, so that the electrosurgical currents are localized between the bare electrode ends 34.

Figure 4:
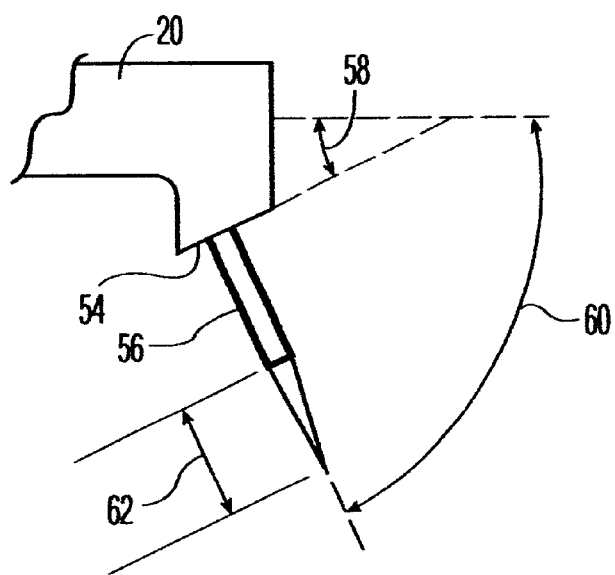
FIG. 4 is a side view of the working end of the probe showing a preferred variant.

In the first embodiment, the needles projected from the working end of the handle at an angle of about 90°. FIG. 4 shows a preferred variant where the needles 56 having the uncoated sections project downwardly and more forwardly such that the angle 60 between the handle axis (horizontal in FIGS. 1 and 4) and the needles is about 75°. This in a preferred embodiment can easily be attained by sloping the bottom end 54 of the handle to form an angle 58 of about 15° with the handle axis. The interior construction remains the same. The advantage of the about 75° degree angle is that it facilitates the insertion of the uncoated needle sections into the tonsillar tissue. Preferably, the length 62 of the uncoated needle sections in this preferred embodiment is about 1.5 cm. In the drawings showing the needles, the needle lengths are not to scale, as the uncoated sections are considerably longer than the coated sections.

The apparatus used in the procedure preferably generates electrosurgical currents with a frequency of about 1.5–4 MHz, with 4 MHz preferred. It is found that this frequency range provides a more controlled lesion size at a lower tissue temperature for greater reproducibility. In the preferred example, the apparatus HEMO setting is preferably chosen as it produces a partially-rectified RF waveform for reduced cutting.

The electrode described has particular utility for shrinking tonsil tissue.

The preferred embodiment of FIG. 1 shows a cable 14 hardwired to the handle 18. This is not essential to the invention. The cable 14 at the end can be replaced by an electrical connector to which a removable cable can be connected and the opposite cable end plugged into the electrosurgical apparatus. As another variation, the interior handle construction which provides electrical connections between the bipolar cable end and the twin needles in front can be replaced by other electrical arrangements, such as electrically-insulated twin brass tubes extending the full length of the handle and into the ends of which are respectively embedded one of the needles to maintain their bipolar nature.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A bipolar electrosurgical probe for volumetric shrinkage of tonsil tissue comprising:

a) an elongated insulated handle having a straight axis and having at a first end means for connecting to a bipolar outlet of electrosurgical apparatus and having at a second end two laterally-spaced needles that have straight bare ends with sharpened points for submucosal penetration of tonsil tissue, b) the bare ends having a length of 1.3–1.7 cm, c) the bare ends extending at an angle to the handle axis of 60–90° such as to allow the two bare ends to enter submucosally penetrated tissue so that bipolar electrosurgical currents from the two needles when the electrosurgical apparatus is activated cause volumetric shrinkage of tonsil tissue.

2. The bipolar electrosurgical probe as claimed in claim 1, wherein the angle is 90°.

3. The bipolar electrosurgical probe as claimed in claim 1, wherein the needles are parallel and extend in a plane approximately perpendicular to the handle axis.

4. The bipolar electrosurgical probe as claimed in claim 1, wherein the bare needle ends have a length of about 0.6 inches.

5. The bipolar electrosurgical probe as claimed in claim 4, wherein the bare needle ends are laterally spaced apart about 0.15–0.25 inches.

6. In combination:

i) a bipolar electrosurgical probe for volumetric shrinkage of tonsil tissue comprising:

a) an elongated insulated handle having a straight axis and having at a first end means for connecting to a bipolar outlet of electrosurgical apparatus and having at a second end two laterally-spaced straight parallel needles that have bare ends with sharpened points for submucosal penetration of tonsil tissue, b) the bare ends having a length of 1.3–1.7 cm, c) the bare ends extending at an angle to the handle axis of 90° such as to allow the two bare ends to enter submucosally penetrated tissue so that bipolar electrosurgical currents from the two needles when the electrosurgical apparatus is activated cause volumetric shrinkage of tonsil tissue;

ii) electrosurgical apparatus capable of generating electrosurgical currents in the MHz range and having a bipolar outlet for receiving the means for connecting, iii) the means for connecting being plugged into the electrosurgical apparatus bipolar outlet.

7. The combination of claim 6, wherein the electrosurgical apparatus generates electrosurgical currents with a frequency of 1.5–4 MHz.

8. The combination of claim 7, wherein the bare needle ends have a length of about 0.6 inches, the bare needle ends are laterally spaced apart about 0.15–0.25 inches.

9. A procedure for volumetric shrinkage of tonsil tissue, comprising the steps:

i) providing electrosurgical apparatus capable of supplying electrosurgical currents in the MHz range and having a bipolar outlet for receiving a bipolar connector;

ii) connecting to the bipolar outlet a bipolar electrosurgical probe for radiofrequency thermal ablation, said electrosurgical probe comprising:

a) an elongated insulated handle having a straight axis and having at a first end means for connecting to a bipolar outlet of electrosurgical apparatus and having at a second end two laterally-spaced needles that have bare ends with sharpened points for submucosal penetration of tonsil tissue, b) the bare ends having a length of 1.3–1.7 cm, c) the bare ends extending at an angle to the handle axis of 60–90° such as to allow the two bare ends to enter submucosally penetrated tissue so that bipolar electrosurgical currents from the two needles when the electrosurgical apparatus is activated cause volumetric shrinkage of tonsil tissue;

iii) penetrating submucosally the tonsil tissue to be shrunk with the sharpened points;

iv) activating the electrosurgical apparatus until the penetrated tissue between the needles is damaged causing volumetric shrinkage of the penetrated tissue.

10. The procedure of claim 9, wherein the apparatus generates electrosurgical currents with a frequency of 1.5–4 MHz.

11. The procedure of claim 10, wherein the angle is 90°, the bare needle ends are straight and have a length of about 0.6 inches, the bare needle ends are laterally spaced apart about 0.15–0.25 inches.

12. The procedure of claim 11, wherein step (iii) is carried out by inserting the bare needle ends to their full bare length into the tonsil tissue.

\* \* \* \* \*